United States Patent [19]
Arpaio, Jr. et al.

[11] Patent Number: 4,934,934
[45] Date of Patent: Jun. 19, 1990

[54] DENTAL FILE/REAMER INSTRUMENT

[75] Inventors: Jerry Arpaio, Jr.; Derek E. Heath, both of Johnson City, Tenn.

[73] Assignee: Quality Dental Products, Inc., Johnson City, Tenn.

[21] Appl. No.: 267,074

[22] Filed: Nov. 4, 1988

[51] Int. Cl.⁵ ............................................. A61C 5/02
[52] U.S. Cl. ................................................ 433/102
[58] Field of Search .................. 433/102, 81, 164, 224

[56] References Cited

U.S. PATENT DOCUMENTS

| 1,307,446 | 6/1919 | Kerr | 433/102 |
| 4,299,571 | 11/1981 | McSpadden | 433/102 |
| 4,332,561 | 6/1982 | McSpadden | 433/102 |
| 4,538,989 | 9/1985 | Arpaio, Jr. et al. | 433/102 |

FOREIGN PATENT DOCUMENTS

| 279144 | 10/1913 | Fed. Rep. of Germany | 433/102 |
| 365050 | 1/1921 | Fed. Rep. of Germany | 433/102 |
| 775073 | 12/1934 | France | 433/102 |

Primary Examiner—John J. Wilson
Attorney, Agent, or Firm—Luedeka, Hodges & Neely

[57] ABSTRACT

A dental instrument adapted to be used as a dental file and dental reamer for removing dead or damaged tissue from the root canal of a tooth. The dental compactor instrument is formed with a tapered shank having at least two helical flutes defining at least two continuous helical cutting edges. A helical peripheral land extends between the helical flutes at the periphery of the shank. The cutting edges have a neutral rake angle.

8 Claims, 2 Drawing Sheets

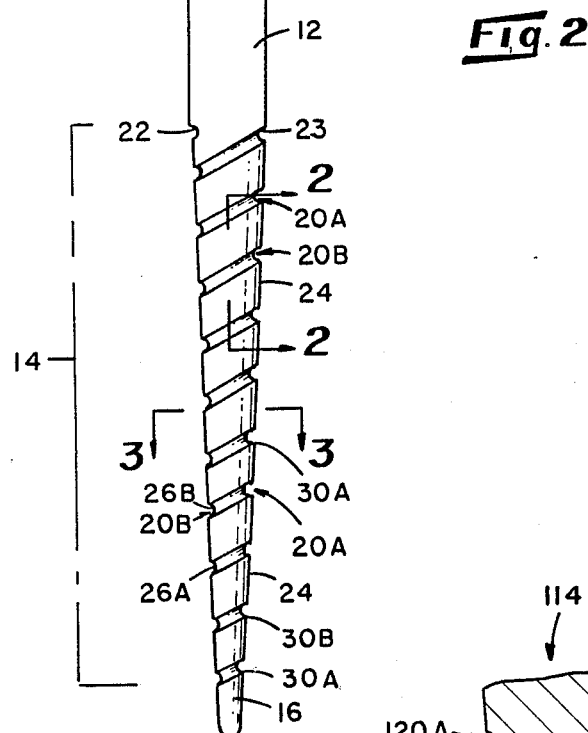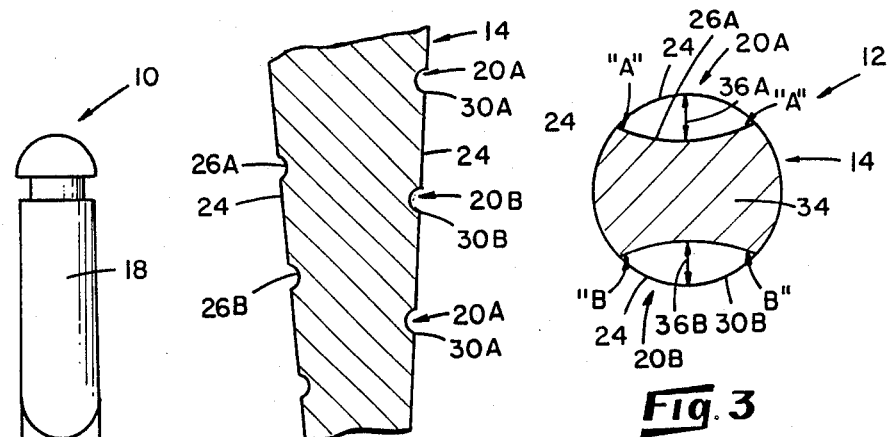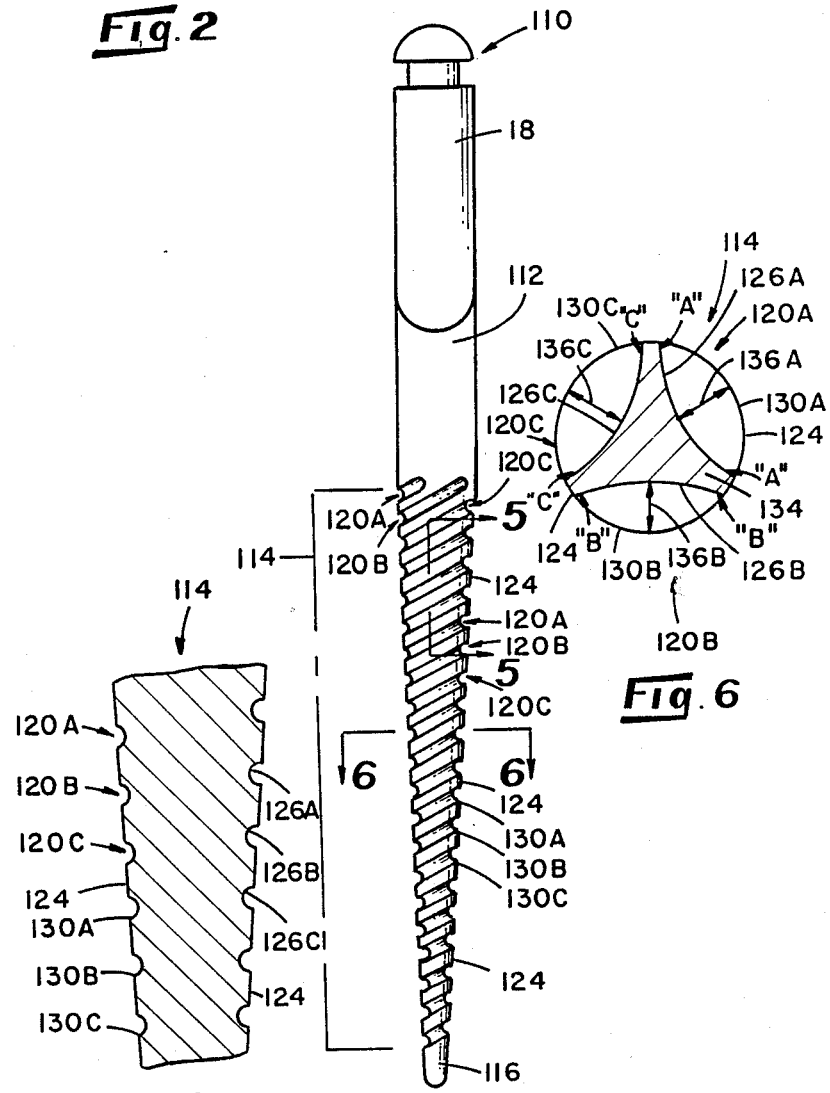

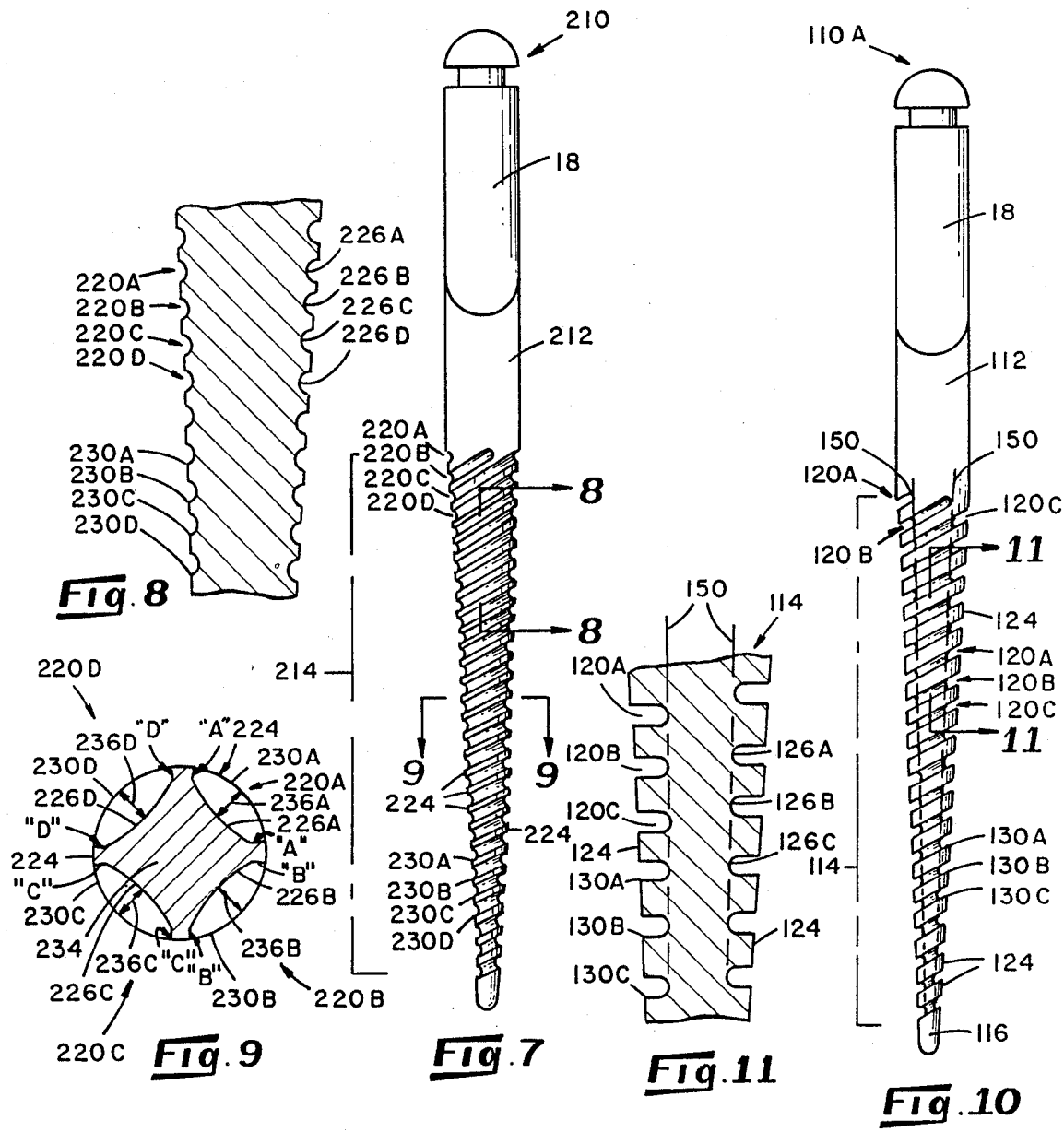

DENTAL FILE/REAMER INSTRUMENT

The present invention relates to the field of dental instruments, and more particularly to dental files and reamers used in endondontia to remove dead or damaged material from a tooth root canal preparatory to filling the root canal.

Extraction of a tooth can often be avoided by removing decayed, damaged, or dead tissue from the root canal of a tooth. Typically, a dentist will first drill into a tooth to locate the root canal and then use a thin, flexible file or reamer instrument to remove the tissue from the root canal. Typically, tooth root canals are not straight, but are curved. Therefore, dental files and reamers must be flexible enough to bend to follow a curved root canal. Dental reamers must also withstand torsional loading exerted on the reamer as it is rotated in one direction to remove the tissue and also withstand reverse torsion loads when rotated in a reverse direction as it is being backed out of a root canal.

One of the widely accepted types of files and reamers are known by the designation K-files and K-reamers. These are made from a tapered rod which may be triangular or square in cross-section. The instruments are fabricated from the rods by twisting to form a generally helical flute along the working portion of the rod. The K-type instruments have several disadvantages. First, the cutting edges formed have a negative rake angle which causes them to have extremely poor tissue removal capacity. Second, they lack flexibility. Finally, because of the method of manufacture, K-instruments tend to break if they become jammed in the root canal and have to be rotated in the opposite direction from that by which they were made due to the stresses set-up during manufacture. A further disadvantage is that when the instruments assume a curved condition to conform to a curved root canal, the tissue removal efficiency on the inside of the curve is increased and on the outside of the curve is decreased. In addition, the attempt of the instrument to return to a straight line configuration causes the tip to dig into the tissue in the region of the tip.

It is an object of the present invention to provide a dental reamer and file which is configured to follow a curved tooth root canal.

It is another object of the present invention to provide a dental file and reamer which is flexible, which has good cutting efficiency, and which has increased torsional strength in both rotational directions about the longitudinal axis of the shank of the instrument.

More particularly, the present invention provides a dental file or reamer instrument having a shank tapered along at least a portion of its length and terminating at a tip end for piloting the shank along a tooth root canal. At least two continuous helical flutes are formed in the tapered portion of the shank defining helical cutting edges with a peripheral land defined between the flutes. The cutting edges have a substantially neutral rake angle.

A more complete understanding of the present invention will be had by reference to the specification and accompanying drawings wherein like numerals refer to like parts throughout and in which:

FIG. 1 illustrates a side view of one embodiment of a dental file or reamer embodying features of the present invention;

FIG. 2 is an enlarged sectional view of the dental file or reamer as seen in the direction of arrows 2—2 in FIG. 1;

FIG. 3 is a transverse cross-sectional view as seen in the direction of arrows 3—3 in FIG. 1;

FIG. 4 illustrates a side view of another embodiment of a dental file or reamer embodying features of the present invention;

FIG. 5 is an enlarged sectional view of the dental file or reamer as seen in the direction of arrows 5—5 in FIG. 4;

FIG. 6 is a transverse cross-sectional view as seen in the direction of arrows 6—6 in FIG. 4;

FIG. 7 illustrates a side view of yet another embodiment of a dental file or reamer embodying features of the present invention;

FIG. 8 is an enlarged sectional view of the instrument as seen in the direction of arrows 7—7 in FIG. 7;

FIG. 9 is a transverse cross-sectional view as seen in the direction of arrows 9—9 in FIG. 7;

FIG. 10 is a modified instrument along the lines of the instrument shown in FIG. 4; and FIG. 11 is an enlarged sectional view as seen in the direction of arrows 11—11 in FIG. 10.

The Figures illustrate a dental instrument used as a file or reamer for removing tissue from the root canal of a tooth. Whether the instrument is a file or a reamer is determined by the pitch of the helical flutes. A greater pitch makes the instrument cut better in the rotary mode, hence a reamer, and a lesser pitch causes the instrument to cut better in the reciprocating mode, hence a file.

With reference to FIGS. 1 through 3, the instrument, generally denoted as the numeral 10, has a shank 12 and a working portion 14 which is tapered along at least a portion of the length of the shank 12 to a tapered pilot end 16. The shank 12 above the working portion 14 is shown as being substantially cylindrical. A fitting 18 is formed on the upper cylindrical part of the shank 12 to connect in a handle for manual manipulation of the instrument (not shown), or to mate with a chuck of a dental handpiece (not shown).

As shown in FIGS. 1 and 2, two continuous helical flutes 20A and 20B are formed in and along the working portion 14 of the shank 12. Hereinafter, the flutes are referred to as a first flute 20A and second flute 20B. The second flute 20B originates at a location denoted as the numeral 22, 180° around the circumference of the shank 12 at the top end of the working portion 14 from the origination region, denoted as the numeral 23, of the first flute 20A. Each flute 20A and 20B is continuous along the length of the working portion 14 to the pilot end 16 of the shank 12.

The first flute 20A and second flute 20B cooperate to define a continuous helical land 24 at the periphery of the working portion 14 of the shank 12 extending between flutes.

With reference particularly to FIG. 2, it can be more clearly seen that the flutes 20A and 20B are each generally U-shaped in transverse cross-section of the flute. That is, the first flute 20A has an arcuately concave wall 26A and the second flute 20B has an arcuately concave wall 26B. The first flute 20A forms a helical cutting edge 30A at the periphery of the shank 12, and second flute 20B forms a helical cutting edge 30B at the periphery of the shank 12.

Now with reference to FIG. 3, there is shown a transverse cross-sectional view of the working portion 14 of the shank 12. The first flute 20A and second flute 20B cooperate to define a web 34 therebetween. The web 34 has a first radial web clearance generally denoted as the numeral 36A from the first cutting edge 30A, and a second radial web clearance, generally denoted as the numeral 36B from the second cutting edge 30B. In transverse cross-section of the shank 12, both the wall 26A of the first flute 20A and wall 26B of the second flute 20B defining the walls of the web 34, are generally concave relative to the periphery of the shank 12. The flute wall 26A of the first flute 20A intersects the periphery of the shank 12 in two regions each denoted by the letter "A" immediately adjacent the shank periphery at an angle of substantially 90 degrees to the tangent of the shank periphery to form what is commonly referred to as a zero or neutral rake angle flute. As shown, each region "A" lays substantially on a radius of the shank 12. The flute wall 26B of the second flute 20B also intersects the periphery of the shank 12 in two regions each denoted by the letter "B" immediately adjacent the shank periphery at an angle of substantially 90 degrees to the tangent of the shank periphery to form what is commonly referred to as a zero or neutral rake angle flute. As shown, each region "B" lays substantially on a radius of the shank 12.

With reference to FIGS. 4–6, there is illustrated a dental instrument 110 similar to the dental instrument 10 of FIGS. 1 through 3 in every respect except that the tapered shank 112 of the instrument 110 is formed with three continuous helical flutes 120A, 120B, and 120C along the tapered working portion 114 of the shank 112. Hereinafter, the flutes are referred to as first flute 120A, second flute 120B, and third flute 120C. The first flute 120A, second flute 120B and third flute 120C each originate at separate locations equally spaced apart around the circumference of the shank 112 at the top end of the working portion. Each flute 120A, 120B and 120C is continuous along the length of the working portion 114 to the pilot end 116 of the shank 112.

The first flute 120A, second flute 120B, and third flute 120C cooperate to define a continuous helical land 124 at the periphery of the working portion 114 of the shank 112 extending between adjacent flutes.

With reference particularly to FIG. 5, it can be more clearly seen that the flutes 120A, 120B, and 120C are each generally U-shaped in transverse cross-section of the flute. That is, the first flute 120A has an arcuate concave wall 126A, the second flute 120B has an arcuate concave wall 126B, and the third flute 120C has an arcuate concave wall 126C. The first flute 120A forms a helical cutting edge 130A at the periphery of the shank 112, the second flute 120B forms a helical cutting edge 130B at the periphery of the shank 112, and the third flute 120C forms a helical cutting edge 130C at the periphery of the shank 112.

Now with reference to FIG. 6, there is shown a transverse cross-sectional view of the working portion 114 of the shank 112. The first flute 120A, second flute 120B and third flute 120C cooperate to define a web 134 therebetween. The web 134 has a first radial web clearance generally denoted as the numeral 136A from the first cutting edge 130A, a second radial clearance generally denoted as the numeral 136B from the second cutting edge 130B, and a third radial clearance generally denoted as the numeral 136C from the third cutting edge 130C. In transverse cross-section of the shank 112, the wall 126A of the first flute 120A, the wall 126B of the second flute 120B, and the wall 126C of the third flute 120C are each generally concave relative to the periphery of the shank 112. The wall 126A of the first flute 120A intersects the periphery of the shank 112 in a region each denoted by the letter "A" immediately adjacent the shank periphery at an angle of substantially 90 degrees to the tangent of the shank periphery to form what is commonly referred to as a zero or neutral rake angle flute. As shown, each region "A" lays substantially on a radius of the shank 112. The wall 126B of the second flute 120B intersects the periphery of the shank 112 in two regions each denoted by the letter "B" immediately adjacent the shank periphery at an angle of substantially 90 degrees to the tangent of the shank periphery to form what is commonly referred to as a zero or neutral rake angle flute. As shown, each region "B" lays substantially on a radius of the shank 112. The wall 126C of the third flute 120C intersects the periphery of the shank 112 in two regions each denoted by the letter "C" immediately adjacent the shank periphery at an angle of substantially 90 degrees to the tangent of the shank periphery to form what is commonly referred to as a zero or neutral rake angle flute. As shown, each region "C" lays substantially on a radius of the shank 12.

With reference to FIGS. 7–9, there is illustrated a dental instrument 210 similar to the dental instrument 10 of FIGS. 1 through 3 in every respect except that the tapered working portion 214 of the shank 212 of the instrument 210 is formed with four continuous helical flutes 220A, 220B, 220C, and 220D along the tapered length of the working portion 214 of the shank 212. Hereinafter, the flutes are referred to as first flute 220A, second flute 220B, third flute 220C, and fourth flute 220D. The first flute 220A, second flute 220B, third flute 220C, and fourth flute 220D each originate at separate locations equally spaced apart around the circumference of the shank 212 at the top end of the working portion 214. Each flute 220A, 220B, 220C and 220D is continuous along the length of the working portion 214 to the pilot end 216 of the shank 212.

The first flute 220A, second flute 220B, third flute 220C and fourth flute 220D cooperate to define a continuous helical land 224 at the periphery of the working portion 214 of the shank 212 extending between adjacent flutes.

With particular reference to FIG. 8, it can be more clearly seen that the flutes 220A, 220B, 220C, and 220D are each generally U-shaped in transverse cross-section of the flute. That is, the first flute 220A has an arcuate concave wall 226A, the second flute 220B has an arcuate concave wall 226B, the third flute 220C has an arcuate concave wall 226C, and the fourth flute 220D has an arcuate concave wall 226D. The first flute 220A forms a helical cutting edge 230A at the periphery of the shank 212, the second flute 220B forms a helical cutting edge 230B at the periphery of the shank 212, the third flute 220C forms a helical cutting edge 230C at the periphery of the shank 212, and the fourth flute 220D forms a helical cutting edge 230D at the periphery of the shank 212.

With reference particularly to FIG. 9, there is shown a transverse cross-sectional view of the working portion 214 of the shank 212. The first flute 220A, second flute 220B, third flute 220C and fourth flute 220D cooperate to define a web 234 therebetween. The web 234 has a first radial web clearance generally denoted as the numeral 236A from the first cutting edge 230A, a second radial clearance generally denoted as the numeral 236B from the second cutting edge 230B, a third radial clearance generally denoted as the numeral 236C from the third cutting edge 230C, and a fourth radial clearance generally denoted as the numeral 236D from the fourth cutting edge 230D. In transverse cross-section of the shank 212, the wall 226A of the first flute 220A, the wall 226B of the second flute 220B, the wall 226C of the third flute 220C, and the wall 226D of the fourth flute 220D are each generally concave relative to the periphery of the shank 212. The wall 226A of the first flute 220A intersects the periphery of the shank 212 in two regions each denoted by the letter "A" immediately adjacent the shank periphery at an angle of substantially 90 degrees to the tangent of the shank periphery to form a zero or neutral rake angle flute. As shown, each region "B" lays substantially on a radius of the shank 212. The wall 226B of the second flute 220B intersects the periphery of the shank 212 in a region denoted by the letter "B" immediately adjacent the shank periphery at an angle of substantially 90 degrees to the tangent of the shank periphery to form a zero or neutral rake angle flute. As shown, each region "B" lays substantially on the radius of the shank 212. The wall 226C of the third flute 220C intersects the periphery of the shank 212 in two regions each denoted by the letter "C" immediately adjacent the shank periphery at an angle of substantially 90 degrees to the tangent of the shank periphery to form a zero or neutral rake angle flute. As shown, each region "C" lays substantially on a radius of the shank 212. The wall 226D of the fourth flute 220D intersects the periphery of the shank 212 in two regions each denoted by the letter "D" immediately adjacent the shank periphery at an angle of substantially 90 degrees to the tangent of the shank periphery to form a zero or neutral rake angle flute. As shown, each region "D" lays substantially on a radius of the shank 212.

In order to increase the flexibility of the instrument the roots of the flutes can be deeper in the areas in which it is desired to increase flexibility. For example, a No. 60 file or reamer can be made to have the flexibility of a No. 40 file or reamer by adjusting the depth of the flutes so that the core approximates that of the smaller sized instrument. Thus, the flutes became deeper as they progress up the shank. In addition to providing increased flexibility, this increases the carrying capacity of the instrument so that the possibility of pushing debris into side canals is minimized.

An example of such an instrument is shown as 110A in FIGS. 10 and 11. The Figures are similar to FIGS. 4 and 5 and have been given the same reference numerals. However, as will be noted by the broken lines 150, the roots of the flutes become deeper as they progress up the shank. Preferably, the included angle between the taper of the working surface of the instrument and the line of the roots of the flutes is from about 1° to 5°. However, it can be varied outside of these limits to obtain special flexibilities or debris carrying capacity.

As shown in FIGS. 1, 4, 7, and 10 the helical flutes are of a right-handed twist and the cutting edges have a right-handed cutting direction.

In order to make any of the above instruments, a tapered blank is rotated and fed across a grinding wheel at a rate which will produce the helical flute. The depth of cut is controlled to produce the substantially 90° cutting edges. It is preferable that the flutes be ground at a constant helix angle which means that pitch will increase as the diameter of the shank increases.

Preferably, to get optimum cutting and guide use, the lands should be from about 0.004 to about 0.006 inches in width. Thus, a No. 40 instrument would have lands about 0.004 inches in width and a flute about 0.020 inches in width. Of course, the width of the flutes will vary with the size of the instrument but the widths of the lands should remain in the range stated. The lands provide a guide means to prevent too deep a cut and minimize the uneven cutting which is observed when a standard K-file or reamer is employed in a curved root canal.

The instrument 10, 110, and 210 can be used as both a dental reamer or a dental file. A dental reamer is used by rotating the instrument in the direction of the twist of the helical flutes, and a dental file is used by reciprocating the instrument in the direction of the longitudinal direction of the shank of the instrument. The primary difference between a dental reamer and a dental file is that the helix angle of the flutes of a dental reamer is steeper, relative to the longitudinal axis of the shank, than is the helix angle of the flutes of a dental file.

The foregoing detailed description is given primarily for understanding of the invention and no unnecessary limitations are to be understood therefrom for modifications will become obvious to those skilled in the art upon reading this disclosure and may be made without departing from the spirit of the invention and scope of the appended claims.

What is claimed is:

1. A dental reamer/file instrument comprising:
   a shank;
   a tapered working portion along at least a portion of the length of said shank;
   flute means formed in the working portion of the shank defining at least two continuous helical flutes having helical cutting edges at the periphery of said working portion of said shank and being equally spaced apart about the circumference of said shank;
   said helical cutting edges have a substantially neutral rake angle at the periphery of said working portion of said shank; and,
   a helical land at the periphery of the working portion of said shank extending between adjacent flutes.

2. The dental reamer/file instrument of claim 1, wherein said helical flute means forms a web having a continuous radial web clearance from the periphery of said working portion, and in transverse cross-section of said working portion the walls of said flutes intersect the periphery of said working portion in a region immediately adjacent said working portion periphery at an angle of substantially 90 degrees to the tangent of said working portion periphery defining the neutral rake angle of said cutting edges.

3. The dental reamer/file of claim 2 wherein the lands are from about 0.004 to about 0.006 inches in width.

4. The dental reamer/file of claim 2 wherein the depth of said flutes increases as the diameter of the shank increases.

5. The dental reamer/file instrument of claim 2, wherein the region of the flute walls defining the neutral rake angle cutting edges lay substantially on a radius of said working portion of said shank.

6. The dental reamer/file of claim 2, wherein said flute means defines four continuous helical flutes having helical cutting edges at the periphery of said working portion of said shank equally spaced about the circumference of said shank.

7. The dental reamer/file instrument of claim 1, wherein the walls of said flute means are generally concave relative to the periphery of said working portion of said shank.

8. The dental reamer/file of claim 2, wherein said flute means defines three continuous helical flutes having helical cutting edges at the periphery of said working portion of said shank equally spaced about the circumference of said shank.

* * * * *